United States Patent
Miyamoto et al.

(10) Patent No.: US 11,118,158 B2
(45) Date of Patent: Sep. 14, 2021

(54) MICROBIAL MATERIAL FOR REDUCING SOIL/WATER QUALITY CONTAMINATION, RESTRICTING WARMING GAS GENERATION, AND IMPROVING PLANT FUNCTION, AND METHOD FOR MANUFACTURING FERMENTATION PRODUCT

(71) Applicants: Japan Eco Science Co., Ltd., Chiba (JP); National University Corporation Chiba University, Chiba (JP); Miroku Co., Ltd., Oita (JP); Keiyo Plant Engineering Co., Ltd., Chiba (JP)

(72) Inventors: Hirokuni Miyamoto, Chiba (JP); Hiroaki Kodama, Chiba (JP); Hisashi Miyamoto, Oita (JP); Takumi Nishiuchi, Ishikawa (JP); Kazuto Ishikawa, Chiba (JP); Kazuo Ogawa, Chiba (JP); Toshiyuki Ito, Chiba (JP); Takuya Kamitai, Sannohe-gun Aomori (JP); Kenshiro Oshima, Chiba (JP); Wataru Suda, Chiba (JP); Masahira Hattori, Chiba (JP)

(73) Assignees: JAPAN ECO SCIENCE CO., LTD., Chiba (JP); NATIONAL UNIVERSITY CORPORATION CHIBA UNIVERSITY, Chiba (JP); MIROKU CO., LTD., Oita (JP); KEIYO PLANT ENGINEERING CO., LTD., Chiba (JP)

( * ) Notice: Subject to any disclaimer, the term of this patent is extended or adjusted under 35 U.S.C. 154(b) by 64 days.

(21) Appl. No.: 16/521,799

(22) Filed: Jul. 25, 2019

(65) Prior Publication Data
US 2020/0017821 A1    Jan. 16, 2020

Related U.S. Application Data

(63) Continuation of application No. 14/901,374, filed as application No. PCT/JP2013/067907 on Jun. 28, 2013, now abandoned.

(51) Int. Cl.
*C12N 1/20* (2006.01)
*C12P 1/04* (2006.01)
*C05F 11/08* (2006.01)

(52) U.S. Cl.
CPC ............ *C12N 1/20* (2013.01); *C05F 11/08* (2013.01); *C12P 1/04* (2013.01)

(58) Field of Classification Search
None
See application file for complete search history.

(56) References Cited

U.S. PATENT DOCUMENTS 9,987,312 B2    6/2018   Miyamoto et al.

FOREIGN PATENT DOCUMENTS

| JP | 3146305 B2 | 3/2001 |
| JP | 3314302 B2 | 8/2002 |

(Continued)

OTHER PUBLICATIONS

International Search Report and Written Opinion for PCT/JP2013/067907.

(Continued)

*Primary Examiner* — Erin M. Bowers
(74) *Attorney, Agent, or Firm* — McClure, Qualey & Rodack, LLP

(57) ABSTRACT

Provided are a functional microbial material and a method for producing a fermentation product, wherein the functional microbial material and the fermentation product are environment-friendly and improve the quality of crops. The present invention relates to a microbial material and a (Continued)

method for producing a fermentation product wherein the microbial material and the fermentation product are obtained by fermentation of a fermentation raw material including a plant-derived raw material and an animal-derived raw material using a population of microorganisms including a plurality of species of thermophilic microorganisms, and lead to a remedy for soil and water pollution and to the inhibition of greenhouse gas generation, as well as contribute to improvements in the functionality of plants, particularly the expression of genes involved in biophylaxis and resistant to high-temperature disorder, and an increase in antioxidant components. Quality enhancement of plants is promoted without genetic recombination, using a population of microorganisms that have a function to restore the environment and a function as an elicitor for the plant. Further, burdens on the natural environment are maintained and restored through normal production activities.

12 Claims, 6 Drawing Sheets

Specification includes a Sequence Listing.

(56) References Cited

FOREIGN PATENT DOCUMENTS

| JP | 3385402 | B2 | | 3/2003 |
|---|---|---|---|---|
| JP | 2003-219864 | | * | 8/2003 |
| JP | 2003-219864 | A | | 8/2003 |
| JP | 2013-141419 | A | | 7/2013 |
| WO | 2011/099514 | A1 | | 8/2011 |
| WO | 2012/124665 | A1 | | 9/2012 |

OTHER PUBLICATIONS

Nautiyal et al., FEMS Microbial. Lett. 182: 291-296 (2000).

Hirokuni Miyamoto et al., "Konetsukin Hakko Sanbutsu ga Shokubutsu Tainai no Amino-san Taisha ni Ataeru Eikyo", Japan Society for Bioscience, Biotechnology, and Agtochemistry Taikai Koen Yo shishu, Mar. 5, 2012, (Mar. 5, 2012), vol. 2012. Web Only, 4C01A07.

Hirokuni Miyamoto et al., "Konetsukin Hakko Sanbutsu ga Shokubutsu no Seicho Sokushin to Seitai Bogyo no Idenshi Hatsugen ni Ataeru Eikyo", Japan Society for Bioscience, Biotechnology, and Agrochemisty Taikai Koen Yo shishu, Mar. 3, 2013, vol. 2013, 2A46A08.

Kazuhito Ishikawa et al., "Konetsukin Hakko Sanbutsu ni yoru Dacchitsu Katei no DGGE Kaiseki", Japan Society for Bioscience, Biotechnology, and Agrochemsitry Takai Koen Yoshishu, Mar. 3, 2012 (Mar. 5, 2012), vol. 2012, Web Only, 4B03A10.

Kazuhito Ishikawa et al., "Konetsukin Hakko Sanbutsu ga Dojo to Shokubutsutaichu no Shosantaichisso Ganryo ni Ataeru Eikyo", Japan Society for Bioscience, Biotechnology, and Agrochemistry Kanto Shibu Jusho Kinen Koen Oyobi Symposium Koen Yoshishu, Sep. 10, 2010, p. 9.

Kazuhito Ishikawa et al., "Konetsukin Hakko Sanbutsu ga Dojo Yurai no Chisso-kei Gas Sansei ni Alaeru Eikyo", Japan Society for Bioscience, Biotechnology, and Agrochemistry Taikai Koen Yoshitsun, Mar. 5, 2011 (Mar. 5, 2011), vol. 2011, p. 1.

* cited by examiner

FIG. 1  Conceptual representation
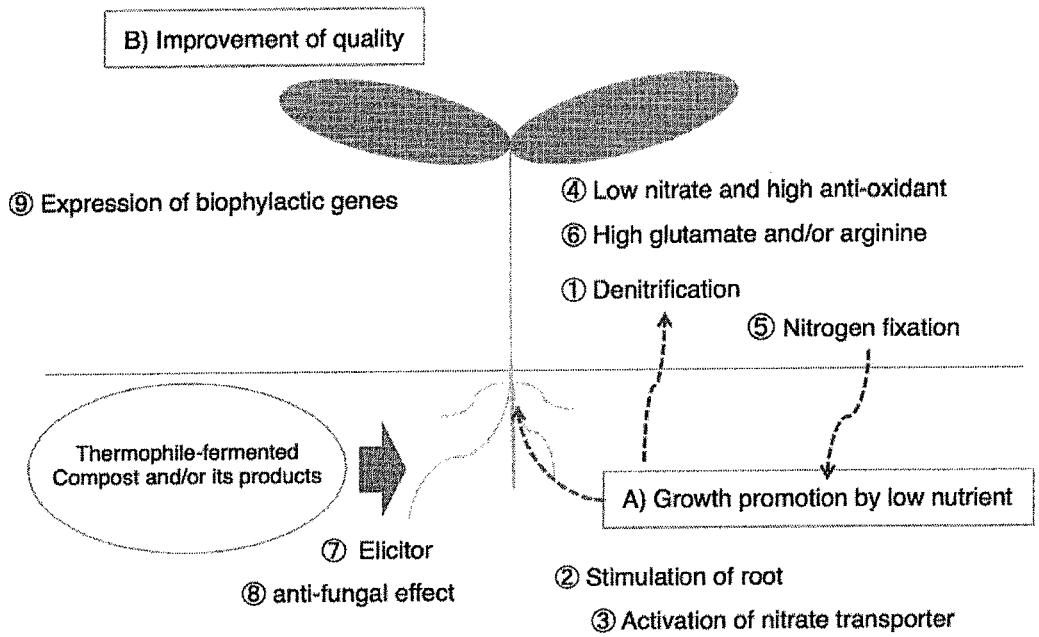
FIG. 2  Bacterial flora (not accepted at NITE) [claim 1]
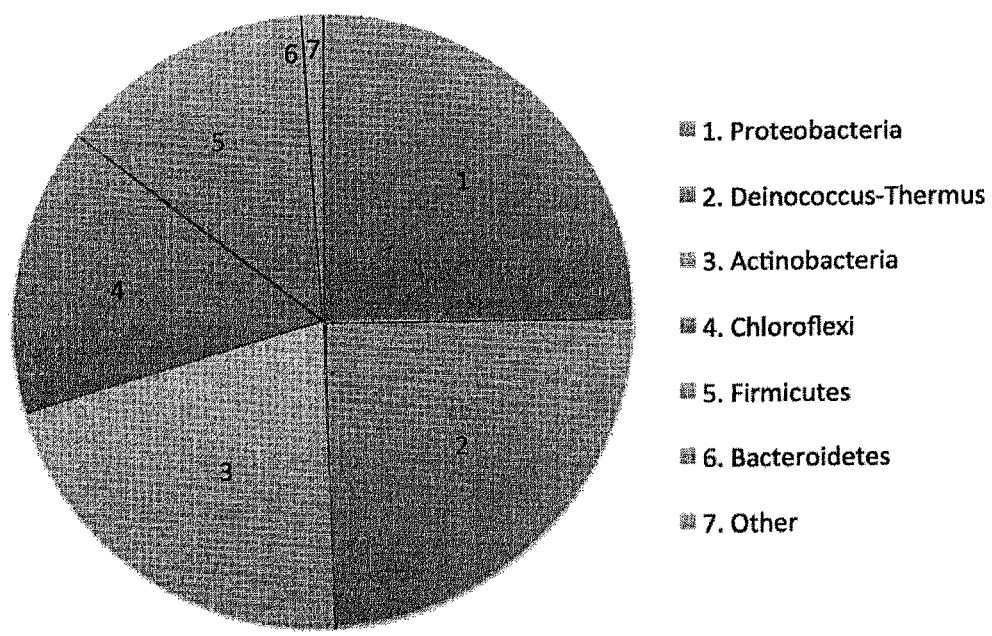

FIG. 3 Effect of decreasing nitrate nitrogen within the plant body (quality improvement): claim 2
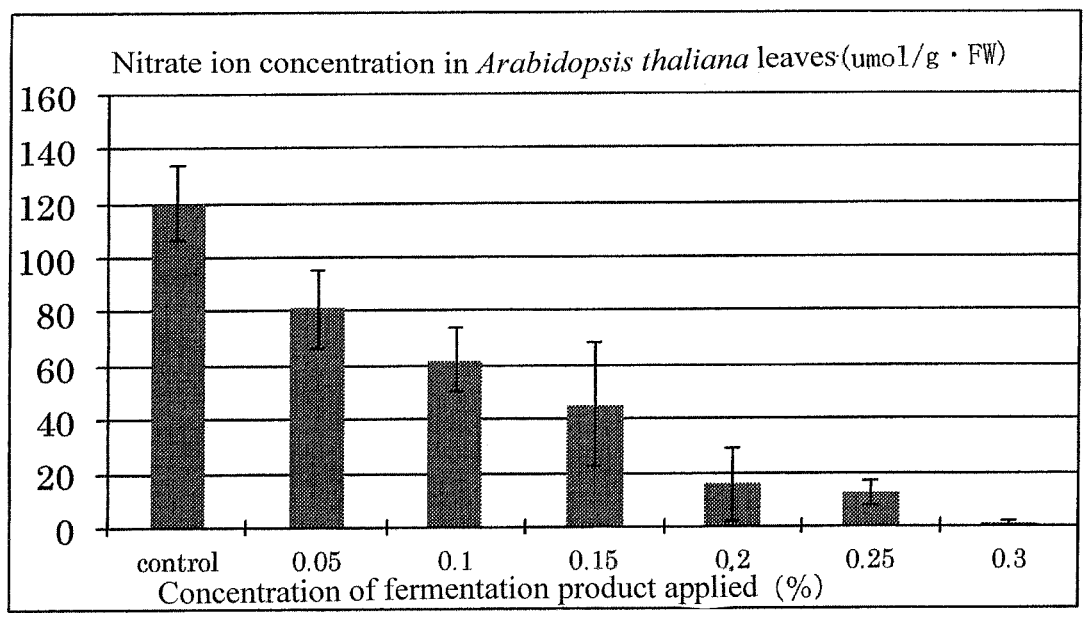
FIG. 4 Effect of decreasing nitrate nitrogen in the soil (effect of reducing groundwater pollution): claim 2
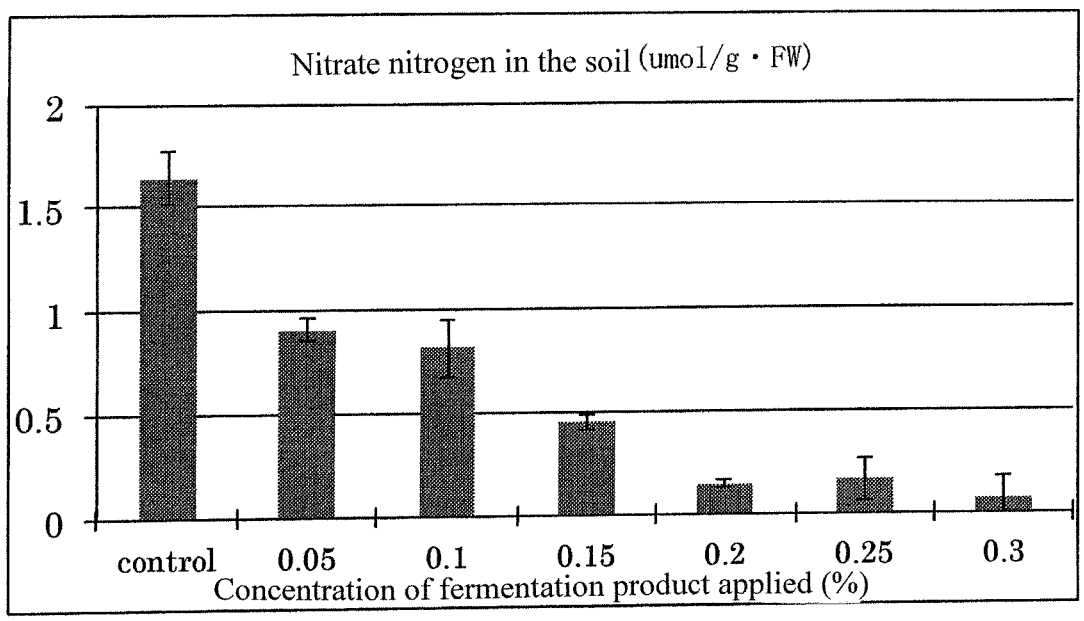

FIG. 5  Effect on the length of *Brassica rapa* var. *perviridis* roots: claim 3
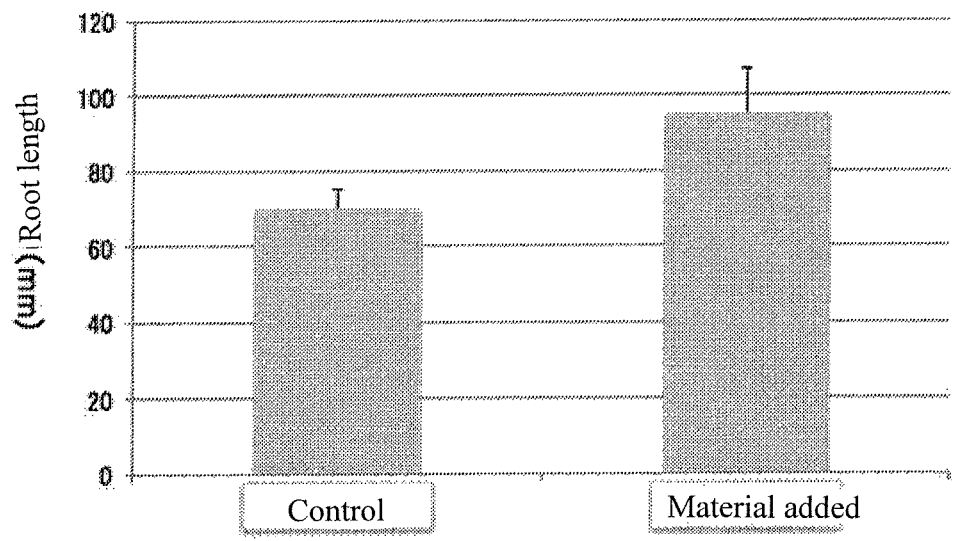
FIG. 6  Effect on the expression of nitrate transporter: claim 3
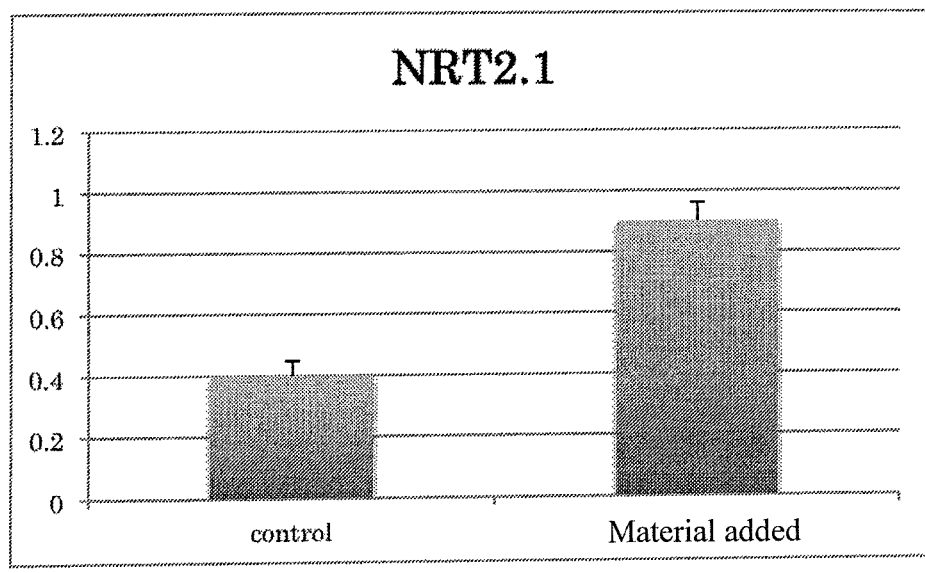

FIG. 7 Nitrate concentration in the soil under acetylene blockage: claim 4
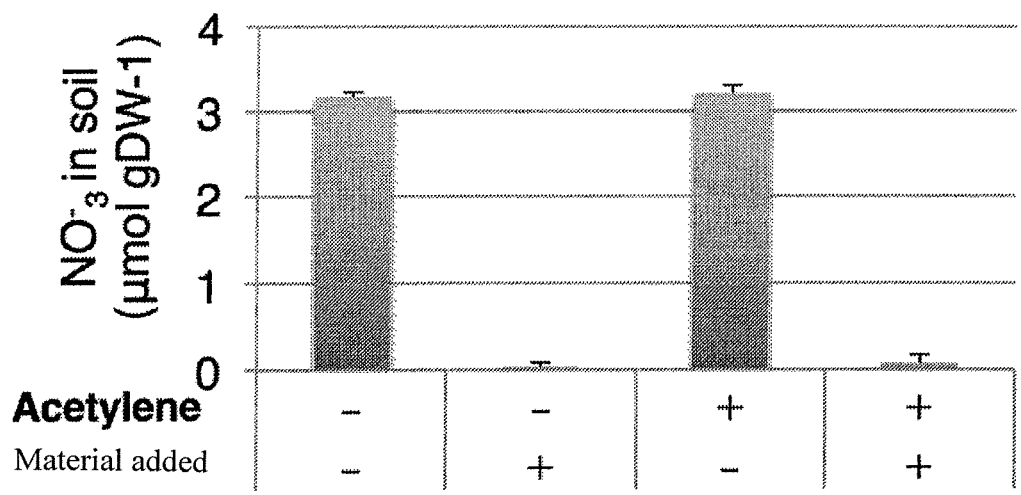
FIG. 8 Detection of N$_2$O under acetylene blockage: claim 4
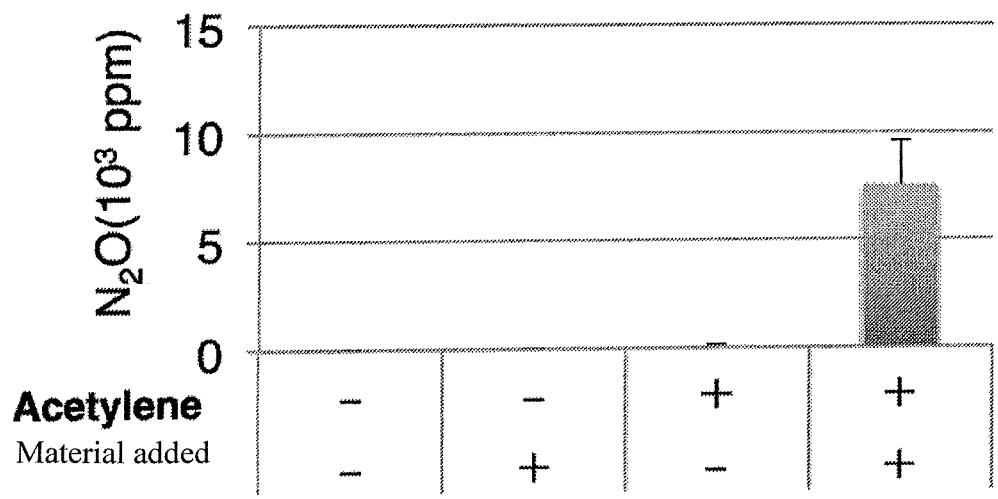

FIG. 9. Ammonium ion concentration in *Arabidopsis thaliana*: claim 4
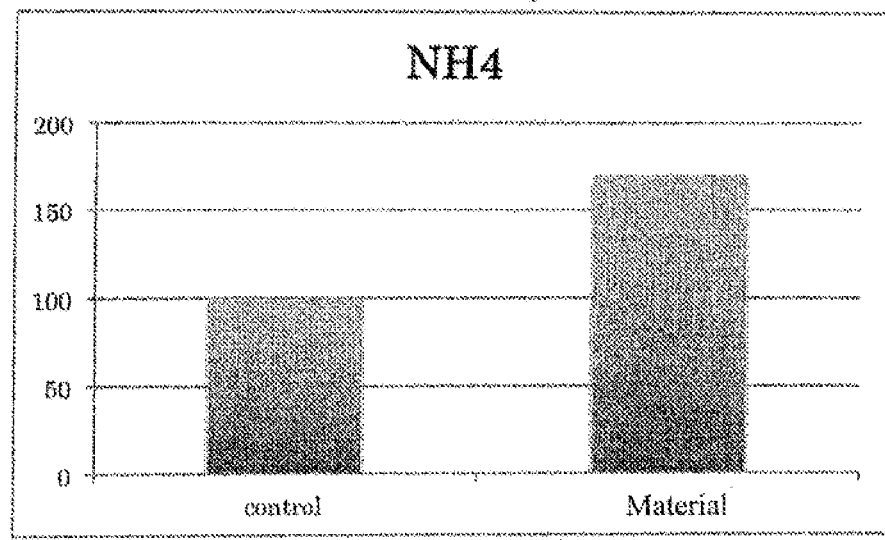
FIG. 10 Glutamine and glutamic acid concentrations in *Arabidopsis thaliana*: claim 5
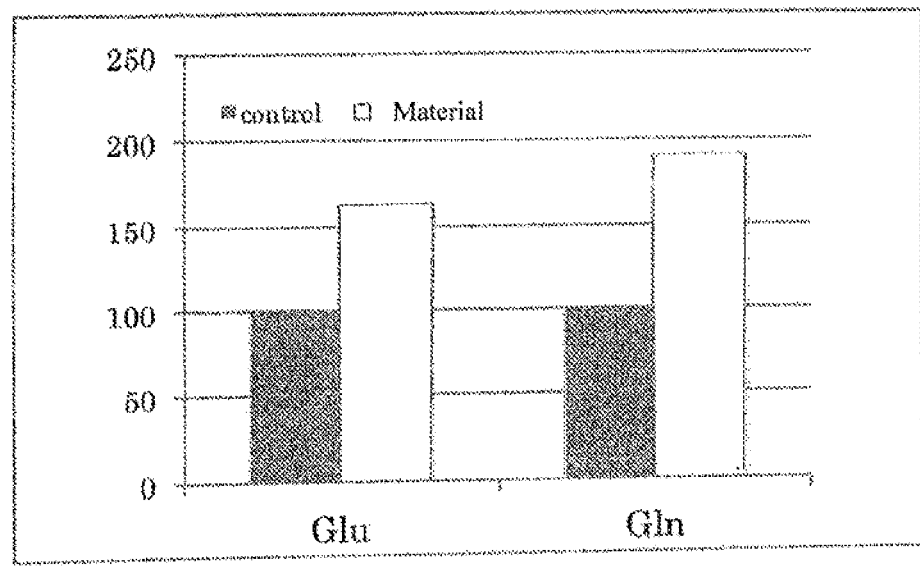

FIG. 11 Proline concentration in *Arabidopsis thaliana*: claims 5 and 6
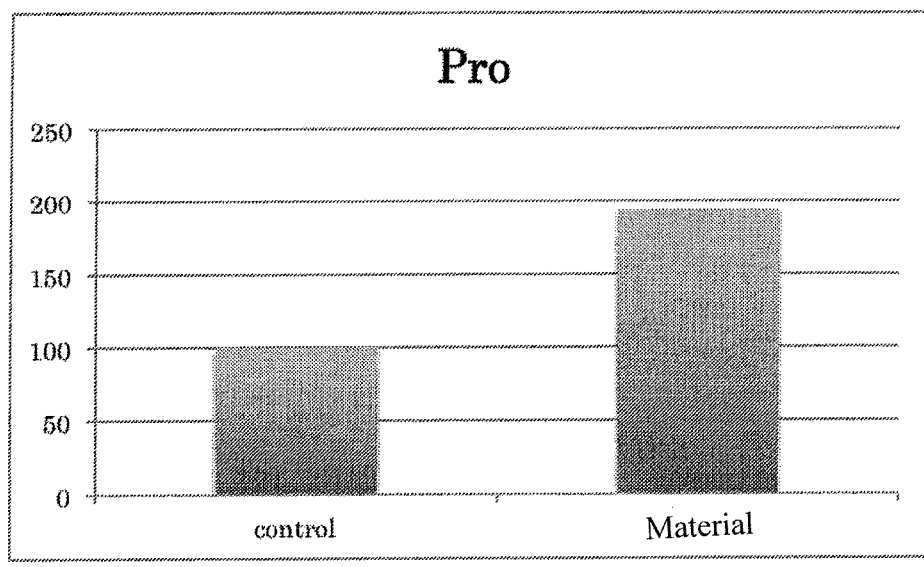
FIG.12
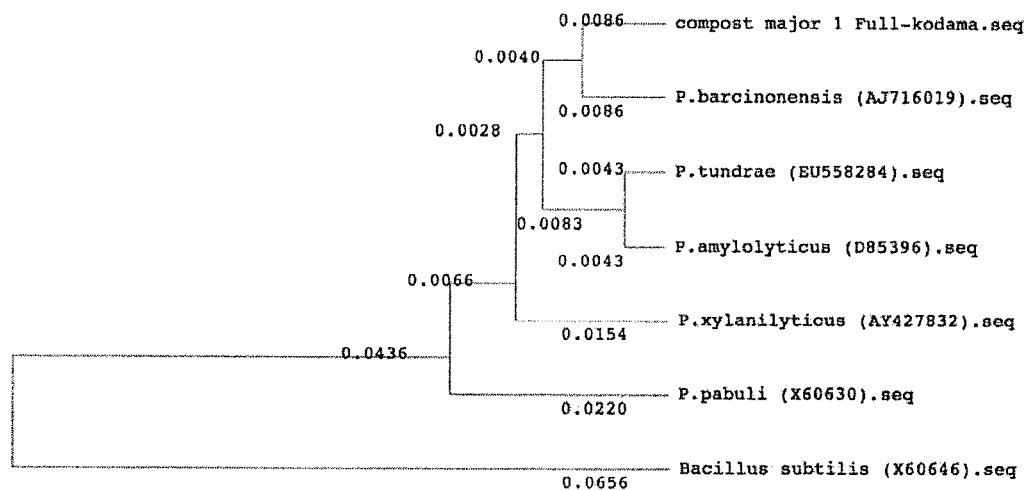

MICROBIAL MATERIAL FOR REDUCING SOIL/WATER QUALITY CONTAMINATION, RESTRICTING WARMING GAS GENERATION, AND IMPROVING PLANT FUNCTION, AND METHOD FOR MANUFACTURING FERMENTATION PRODUCT

CROSS REFERENCE TO RELATED APPLICATIONS

This application is a Continuation of pending U.S. patent application Ser. No. 14/901,374, filed on Dec. 28, 2015, the entirety of which is incorporated by reference herein.

TECHNICAL FIELD

The present invention relates to a microbial material and a method for producing a fermentation product, wherein the microbial material and the fermentation product are obtained by fermentation of a fermentation raw material including a plant-derived raw material and an animal-derived raw material using a plurality of species of thermophilic microorganisms, and lead to a remedy for soil and water pollution and to the inhibition of greenhouse gas generation, as well as contribute to improvements in the functionality of plants, particularly the expression of genes involved in biophylaxis and resistant to high-temperature disorder, and an increase in antioxidant components.

BACKGROUND ART

In recent years, environmental problems become serious on a worldwide scale. For example, looking at agriculture from the perspective of environment, after chemical fertilizers or immature compost has been applied to farmlands, pollution with nitrate ions penetrating into groundwater and generation of dinitrogen monoxide, which is a greenhouse gas, from the soil are regarded as problematic. Effects of global warming cause high-temperature disorder in cultivating of crops and also are an environmental factor triggering the outbreak of diseases. Furthermore, owing to global food problems, techniques are being sought for efficient production of crops. In this context, there is a situation where efficient use of chemical fertilizers or agricultural chemicals is necessary, but these materials are a factor responsible for the above-described environmental destruction. On the other hand, there is a need for agricultural production techniques that are friendly to the environment and health, while there are being carried out improvements in materials and facilities and developments of techniques, such as cleanup techniques (see Patent Literatures 1 to 3). Patent Literature 1 is directed to a foliar spray agent in which an organic acid aqueous solution from sugar fermentation, and magnesium or calcium, and optionally urea are coexistent, so that the above-mentioned problem is solved. In Patent Literature 1, the capability of decreasing nitrate is observed, but this mechanism is unknown and the foliar spray agent exhibits no effects exerted on other environmental aspects and the functionality of plants. Patent Literature 2 is characterized in that the UV source is in the range of wavelength of 280 to 380 nm and has a peak at a wavelength of around 312 nm. In Patent Literature 2, there are provided findings on an optimal control of electric lighting which can be applied only to plant factories based on artificial light, but the UV source does not have any effects exerted on other functionality of plants. Patent Literature 3 is directed to a method for decreasing nitrate nitrogen and volatile organic compounds using an alcohol. Patent Literature 3 is related to a technique for decreasing nitrate and volatile organic compounds from a soil, but the use of an alcohol and the like does not allow this technique to be applied to agricultural field sites.

In addition, molecular mechanisms by which plants can deal with poor environmental conditions have been elucidated (see Non-Patent Literatures 1 to 5); however, some of techniques utilizing these mechanisms are ones like genetic recombination techniques, which are difficult to be accepted in the society (Non-Patent Literatures 6 to 8). Non-Patent Literatures 1 to 5 provide findings on the involvement of HSPs associated with properties resistant to diseases and high-temperature disorder, but none of these discloses an overall assessment of effects on the body of plants, for example, unlike the present invention. Non-Patent Literatures 6 to 8 provide findings on genetic recombination techniques, and it cannot be said that as provided by the present invention, these provide a technique having multi-faceted functions, such as a decrease in nitrate, an increase in the amounts of antioxidant substances, biophylactic functions, and resistance to high-temperature disorder, without genetic recombination.

Meanwhile, the present inventors have developed fermentation materials using a population of microorganisms including a plurality of species of thermophilic microorganisms, such as *Bacillus brevis* and *Bacillus stearothermophilus, Thermopholic actinomycetes*, and species closely related thereto (see Patent Literatures 4 to 7).

CITATION LIST

Patent Literatures

Patent Literature 1: JP 2006-036684 A
Patent Literature 2: JP 2008-086272 A
Patent Literature 3: JP 2002-370085 A
Patent Literature 4: JP 3146305 B1
Patent Literature 5: JP 3314302 B1
Patent Literature 6: JP 3385402 B1
Patent Literature 7: WO 2011/099514

Non-Patent Literatures

Non-Patent Literature 1: Jaroszl D F and Susan Lindquistl S. (2010) Hsp90 and Environmental Stress Transform the Adaptive Value of Natural Genetic Variation. Science 330: 1820-1824.
Non-Patent Literature 2: Yule Liu et al. (2004) Molecular Chaperone Hsp90 Associates with Resistance Protein N and Its Signaling Proteins SGT1 and Rar1 to Modulate an Innate Immune Response in Plants. J. Biol. Chem. 279: 2101-2108.
Non-Patent Literature 3: Jae-Heung K et al. (2000) Upregulation of an *Arabidopsis* RING-H2 gene, XERICO, confers drought tolerance through increased abscisic acid biosynthesis. The Plant Journal 47: 343-355.
Non-Patent Literature 4: Snyman M and Cronje M J. (2008) Modulation of heat shock factors accompanies salicylic acid-mediated potentiation of Hsp70 in tomato seedlings. Journal of Experimental Botany 59: 2125-2132.
Non-Patent Literature 5: William B. Gurley (2000) HSP101: A Key Component for the Acquisition of Thermotolerance in Plants. The Plant Cell, Vol. 12, 457-460.
Non-Patent Literature 6: Enikeev A G et al. (2010) Tobacco cell cultures transformed by the hsp 101 gene exhibit an increased resistance to potassium fluoride Dokl Biol Sci 430: 29-30.

Non-Patent Literature 7: Montero-Barrientos M et al. (2010) Transgenic expression of the *Trichoderma harzianum* hsp70 gene increases *Arabidopsis* resistance to heat and other abiotic stresses. J Plant Physiol 167: 659-65.

Non-Patent Literature 8: Prieto-Dapena P et al. (2006) Improved resistance to controlled deterioration in transgenic seeds. Plant Physiol 142: 1102-12.

SUMMARY OF THE INVENTION

Technical Problems

Conventional agriculture makes excessive use of chemical fertilizers, which as a result, causes problems leading to the pollution with nitrate penetrating into groundwater and to the generation of a greenhouse gas dinitrogen monoxide produced by molds propagated in agricultural lands. In addition, it has become problematic that with global warming, high-temperature disorder and diseases of crops are triggered. Therefore, there is a need for a technique that is friendly to the environment and improves the quality of crops.

The present invention is to provide a functional microbial material to solve the above-described problems. Soil and water environments have factors that always vary, and thus it is necessary that to these varying factors, multifunctional effects are exhibited by a population of multiple species of microorganisms, not by a single species of microorganism. For example, taking, as an example, a soil that allows the growth of a crop, a period of rainfall leads to an increased content of water in the soil, whereas a period of low rainfall makes the soil rather dry. Depending on these variations, stable multiple responses are made to achieve an improvement in and modification of functions of plants.

Solution to Problems

I. Effects which the Thermophilic Bacteria Fermentation Product has on Soil and Groundwater Pollution and on Greenhouse Gas Generation 1. The concentration of nitrate ions in the soil is decreased.

2. This reaction is inhibited by microorganisms having high sensitivity to antibiotics such as chloramphenicol (and their enzymes).

3. The reaction of denitrification from the soil is promoted. In particular, the production of $N_2O$ is suppressed and the production of $N_2$ is promoted. $N_2O$ gas has a warming potential about 300 times higher than $CO_2$, and thus it is important to suppress its generation. This reaction is thought to be promoted by P450nor derive from fungi; the fermentation product according to the present invention (a microorganism strain NP-1 contained therein) has a function of suppressing fungous growth and further results in functioning of a group of genes that leads to preferential denitrification of $N_2$ gas.

4. As a result, the reactions described above also reduce water pollution with nitrate penetrating from the soil into groundwater.

5. It is possible that the water cleanup of polluted water having a high salt concentration (of around 10%) is achieved by means of halotolerant and alkali-resistant bacteria (of the genera *Oceanobacillus* and *Virgibacillus*).

II. Effects which the Thermophilic Bacteria Fermentation Product has on the Functionality of Plants 1. The action of thermophilic bacteria results in the activation of nitrate transporters in roots and efficient use of nitrate in the soil.

2. Root hairs are developed, and their growth is promoted by, for example, the activation of auxins.

3. The reactions described above lead to efficient use of nitrogen from the soil, allowing increased production with small amounts of nitrogen.

4. Heat-resistant plants are grown by enzymatic repair functions by a group of HSPs.

5. Crops rich in antioxidants are provided by increases in glutathione transferase, vitamins A, C, and E, and others.

6. The outbreak of plant pathogens and insect pests is inhibited by the activation of LTPs, protease inhibitors, and others.

The functional material according to the present invention is based on a fermentation raw material that may be made up of about 70% to about 80% by weight of a plant-derived raw material and about 30% to about 20% by weight of an animal-derived raw material.

In addition, the functional material according to the present invention can be obtained by fermentation using a population of microorganisms including a population of microorganisms designated by the deposition number NITE BP-1051. The functionality of the functional material is stabilized, for example, by a population of microorganisms designated by the deposition number ATCC PTA-1773.

Further, the population of microorganisms contained in the functional material according to the present invention can have $10^8$ cells/g to about $10^9$ cells/g.

The plant-derived raw material which is used for a functional material according to the present invention can be one or more selected from the group consisting of rice bran, barley and like bran, broken husks, soybean cake, bean curd refuse, sakekasu (sake lees), shochu (distilled spirit) lees, tea leaves residuals, coffee grounds, residues after squeezing fruits, and residues after squeezing vegetables. The animal-derived raw material which is used in the present invention can be one or more selected from the group consisting of crustaceans, fishes, and residues after processing crustaceans, and residues after processing fishes.

Another functional material according to the present invention is a functional material containing about 1% to about 5% by weight of the functional material as described above.

The present invention further relates to a method for producing a functional material, the method including the stirring step of stirring a plant-derived raw material and an animal-derived raw material to obtain a fermentation raw material; and a fermentation step of subjecting the fermentation raw material obtained by the stirring step to fermentation using a population of microorganisms designated by the deposition number ATCC PTA-1773.

Advantageous Effects of Invention

According to the present invention, as shown in FIG. 1, a group of highly stable enzymes in a population of active microorganisms within the material according to the present invention brings about denitrification of nitrate ions in a soil without the penetration of the nitrate ions into the ground, as nitrogen gas, and by using its stimulus and the like, rooting is induced and nitrate transporters in roots are activated. This results in the growth of plants even under conditions of low nutrients, and decreased concentrations of nitrate within the body of plants, as well as increased amounts of components having high antioxidation activity. In addition, active microorganisms themselves within the material and a population of active microorganisms in a soil that is activated by the active microorganisms bring about the fixation of nitrogen gas in the soil and in the air in symbiosis with the plant, resulting in increased concentrations of glutamic acid, arginine, and others within the plant body. Furthermore, effects that are provided by, for example, components of the cell wall of highly stable microorganisms within the material result in increased amounts of expression of genes involved in biophylaxis and resistant to stresses of plants themselves. At the same time, effects exerted by, for example, cyclic lipopeptides and heat-resistant enzymes secreted by microorganisms within the material inhibit the growth of filamentous fungi with high pathogenicity, and by and large, improve the quality and functions of plants. Results of these mechanisms of action are as follows. 1) It becomes possible to inhibit nitrate pollution in soils and water and the generation of a warming $N_2O$ gas emitted into the air, as effects exerted on soil and groundwater pollution, water pollution, and greenhouse-gas production. In industrial wastewater, it also becomes possible to carry out the treatment of wastewater in an environment with high salt concentration and high alkalinity, which has been difficult to clean up, by using properties of halotolerant and alkali-resistant bacteria. 2) It becomes possible, as effects that the thermophilic bacteria fermentation product has on the functionality of plants, to provide a reduced function of nitrification and increase the production of antioxidant substances at high concentrations. At the same time, it is possible to avoid high-temperature disorder by HSPs and others enhancing enzymatic repair function in crops and achieve the activation of the biophylaxis system against environmental stresses, such as enhanced repellency to insect pests, by effects exerted by LTPs, protease inhibitors, and others.

BRIEF DESCRIPTION OF THE DRAWINGS

FIG. 1 is a schematic representation showing effects that a functional microbial material according to the present invention has on a soil, a plant, and the environment.

FIG. 2 is a pie chart showing the bacterial phyla in a system of multiple microorganisms when a functional material according to the present invention has been stabilized.

FIG. 3 is a graph showing the effect of decreasing nitrate within the plant body, which is dependent on the amount of addition of a functional material according to the present invention. The graph indicates changes in the concentration of nitrate within the body of a model plant, *Arabidopsis thaliana*.

FIG. 4 is a graph showing the effect of decreasing nitrate in a soil, which is dependent on the amount of addition of a functional material according to the present invention, and indicates changes in the concentration of nitrate in the soil.

FIG. 5 is a graph of experimental results showing the length of roots of komatsuna (*Brassica rapa* var. *perviridis*) cultivated with a functional material according to the present invention.

FIG. 6 is a graph of experimental results showing the amount of expression of a nitrate transporter in roots of a plant *A. thaliana* cultivated with a functional material according to the present invention.

FIG. 7 is a graph of experimental results showing changes in the concentration of nitrate in a soil when a functional material according to the present invention was used and when an acetylene block method was carried out.

FIG. 8 is a graph of experimental results showing the concentration of $N_2O$ produced in a soil and accumulated when a functional material according to the present invention was used and when an acetylene block method was carried out.

FIG. 9 is a graph of experimental results showing the concentration of ammonium ions accumulated within the body of a plant *A. thaliana* when a functional material according to the present invention was used.

FIG. 10 is a graph of experimental results showing the concentrations of glutamic acid and glutamine within the body of a plant *A. thaliana* when a functional material according to the present invention was used.

FIG. 11 is a graph of experimental results showing the concentration of proline accumulated within the body of a plant *A. thaliana* when a functional material according to the present invention was used.

FIG. 12 represents a phylogenetic tree of 16S rRNA base sequences from several strains including the new *Paenibacillus* strain.

DESCRIPTION OF EMBODIMENTS

The following gives a description of embodiments for carrying out the present invention. The present invention is not limited to these embodiments.

The present invention provides a functional microbial material wherein the microbial material is obtained by fermentation of a fermentation raw material including a plant-derived raw material and an animal-derived raw material using a population of microorganisms including a plurality of species of thermophilic microorganisms, and leads to a remedy for soil and water pollution and to the inhibition of greenhouse gas generation and at the same time, has a function of contributing to an improvement in the functionality of plants.

The population of microorganisms and their metabolic products that are included in a functional material according to the present invention are thought to modify the circulation of nitrogen into a soil, groundwater, plants, and the air by acting on the microflora in the soil to which the functional material has been applied and modifying nitrate reduction reactions in the soil, as well as denitrification reactions. It is also thought that changes in the soil microflora lead to changes in the gene expression pattern in plants and induction of heat shock proteins (HSPs), antioxidant components, and others.

The population of microorganisms which can be used in the present invention includes a plurality of species of thermophilic microorganisms. Specific species of these microorganisms include, for example, *Bacillus brevis, Bacillus stearothermophilus, Bacillus thermoamylovorans, Thermopholic actinomycetes*, and species closely related thereto. Among these species, it is preferable that the population of microorganisms which is used in the present invention includes a population of microorganisms designated by the deposition number ATCC PTA-1773 and a population of microorganisms designated by the deposition number BP-1051.

The population of microorganisms designated by the deposition number ATCC PTA-1773 is a mixture of microorganisms including a thermophilic bacterium C-1, which is a species closely related to *Bacillus brevis*, a thermophilic bacterium C-3, which is a species closely related to *Bacillus brevis*, and a thermophilic bacterium CH-4, which is a species closely related to *Bacillus stearothermophilus*, a thermophilic actinomycete MH-1, a thermophilic or heat-resistant lactobacillus LM-1, which is a species closely related to *Bacillus coagulans*, and a thermophilic or heat-resistant lactobacillus LM-2, which is a species closely related to *Bacillus coagulans*.

It is preferable that a functional material according to the present invention includes a population of microorganisms of from about $10^8$ cells/g to about $10^9$ cells/g. It is further preferable that a functional material according to the present invention includes a population of microorganisms designated by the deposition number ATCC PTA-1773 of from about $10^8$ cells/g to about $10^9$ cells/g; and a population of microorganisms designated by the deposition number NITE BP-863 of from about $10^6$ cells/g to about $10^7$ cells/g.

It is preferable that the microbial material which is used in the present invention includes 10% to 1% by weight of a population of microorganisms designated by the deposition number NITE BP-1051. The population of microorganisms includes thermophilic microorganisms of the genera *Bacillus, Lysinibacillus, Virgibacillus, Anoxybacillus*, and *Paenibacillus*. Further, the microbial material is stabilized by the co-existence with Thermophiles inoculum MIROKU M2K including microorganisms of the genera *Meiothermus, Vulcanithermus, Thermus, Oceanobacillus*, and the like in the phylum *Deinococcus-Thermus*. Thermophiles inoculum MIROKU M2K, which is a population of these microorganisms, was not accepted for deposition at the National Institute of Technology and Evaluation because it is a mixture of bacteria of multiple species and is difficult to culture, and thus has been stored at Miroku Co., Ltd. (Kitsuki, Oita Pref.). The population of microorganisms that has been deposited at the ATCC under the deposition number PTA-1773 can also be utilized as a population of microorganisms that can be co-existent as in this case.

The plant-derived raw material that is used in the present invention refers to a raw material derived from plants such as vegetables and grains, and can be inexpensive raw materials, for example, food scraps and others. In particular, the plant-derived raw material includes, for example, rice bran, barley and like bran, broken husks, soybean cake, bean curd refuse, sakekasu (sake lees), shochu (distilled spirit) lees, tea leaves residuals, coffee grounds, residues after squeezing fruits, and residues after squeezing vegetables.

The animal-derived raw material that is used in the present invention refers to a raw material derived from animals such as fishes and crustaceans. In particular, the animal-derived raw material includes, for example, crustaceans, fishes, and residues after processing them.

As crustaceans, use can be made of organisms referred to as shrimp, crab, hermit crab, and the like. As fishes, use can be made of bottom fishes that have been caught in trawls, fishes which have been caught by fishing but are not sold in markets, and others. Further, residues of crustaceans and fishes after they have been processed for foods can also be used.

The fermentation raw material that is used in the present invention is preferably made up of about 50% to about 90% by weight of a plant-derived raw material and about 50% to about 10% by weight of an animal-derived raw material, and further preferably about 70% to about 80% by weight of a plant-derived raw material and about 30% to about 20% by weight of an animal-derived raw material.

A functional material according to the present invention is capable of improving the functionality of plants, while remedying soil and water pollution and inhibiting greenhouse gas generation.

The present invention further provides a method for producing the above-described functional microbial material. The method for producing the functional material includes (a) the stirring step of stirring a plant-derived raw material and an animal-derived raw material to obtain a fermentation raw material; and (b) a fermentation step of subjecting the fermentation raw material obtained by the stirring step to fermentation using a population of microorganisms designated by the deposition number NITE BP-1051.

The stirring step (a) according to the present invention is a step in which a plant-derived raw material as described above and an animal-derived raw material as described above are stirred and mixed to obtain a fermentation raw material having the respective raw materials dispersed approximately uniformly therein. In the case of the fermentation raw material that is incomplete in dispersing these raw materials, fermentation in the subsequent fermentation step could become incomplete. It is also preferable to grind the plant-derived or animal-derived raw material prior to the stirring, because grinding of the raw material leads to easy stirring of these raw materials.

The fermentation step (b) according to the present invention is a step in which the fermentation raw material obtained in the stirring step (a) is subjected to fermentation. In the fermentation, use is made of a population of microorganisms designated by the deposition number NITE BP-1051. The temperature of fermentation is preferably about 20° C. to about 90° C., further preferably about 30° C. to about 50° C. The period of fermentation is preferably about 5 hours to about 24 hours, further preferably about 10 hours to about 14 hours.

In addition, the fermentation step (b) is preferably carried out using at least two fermentation vessels. In cases using a plurality of fermentation vessels, it is preferable that the fermentation temperatures at the respective stages in the fermentation vessels are varied. This is because at each of these stages, fermentation is carried out with microorganisms having a preference to the temperature at the stage, thereby making it possible to obtain a functional microbial material that is produced by multiple fermentation reactions.

TABLE 1

Population of microorganisms that has been internationally deposited as NITE BP-1051: claims 7 and 8

| No. | deposit no. | Closely related species |
|---|---|---|
| IP-95 | AB618495 | *Bacillus ruris* LMG 22866$^T$ |
| IP-2 | AB618496 | *Bacillus badius* NBRC 15713$^T$ |
| IP-14 | AB618497 | *Bacillus fortis* LMG 22079$^T$ |
| N-16 | AB618492 | *Bacillus coagulans* ATCC7050$^T$ |
| IP-23 | AB618498 | *Lysinibacillus xylanilyticus* KCTC 13423$^T$ |
| IP-9 | AB618499 | *Virgibacillus pantothenticus* IAM 11061$^T$ |
| IP-3 | AB618500 | *Anoxybacillus kamchatkensis* DSM 14988$^T$ |
| IP-60 | AB618501 | *Paenibacillus timonensis* CIP 108005$^T$ |
| IP-75 | AB618502 | *Paenibacillus curdlanolyticus* IFO 15724$^T$ |

Table 1 indicates species closely related to bacteria BP-1051 internationally deposited at the NITE, and their sequence registration.

TABLE 2

Thermophiles inoculum MIROKU M2K (Closely related species of bacteria genera identified on the basis of the results of analysis of 16S rDNA sequences)
Genus listing Achromatium
Acidimicrobineae
Acidimicrobium
Actinomyces
Adhaeribacter
Aeriscardovia
Aeromicrobium
Afifella
Alicyclobacillus
Allofustis
Amphibacillus
Anaerococcus
Anaerococcus
Anaerovorax
Anoxybacillus
Atopostipes
Atopostipes
Bacillaceae bacterium
Bacillus
Bacteroides
Barnesiella
Bifidobacterium
Brachybacterium
Brevibacterium
Caldanaerobacter
Caldicellulosiruptor
Caldilinea
Caloramator
Cellulosimicrobium
Cerasibacillus
Clostridiales bacterium
Clostridium
Coprothermobacter
Corynebacterium
Craurococcus
Curtobacterium
Desulfotomaculum
Desulfurispora
Dietzia
Dorea
Eubacterium
Flavobacterium
Gammatimonas
Geobacillus
Georgenia
Gordonia
Gracilibacillus
Halorhodospira
Heliobacterium
Hippea
Hydrogenophilus
Jeotgalicoccus
Lactobacilius
Leucobacter
low G + C Gram-positive bacterium
Lutispora
Macrococcus
Mahella
Marinibacillus
Mechercharimyces
Maiothermus
Methylocystis
Methylosinus
Microbacterium
Micrococcineae
Moorella
Mycobacterium
Nisaee
Nosocomiicoccus
Oceanobacillus
Paenibacillus
Parabacteroides
Pediococcus
Peptoniphilus
Pheaospirillum TABLE 2-continued Thermophiles inoculum MIROKU M2K (Closely related species of bacteria genera identified on the basis of the results of analysis of 16S rDNA sequences)
Genus listing Propionibacterineae
Prosthecomicrobium
Rhodospirillum
Roseiflexus
Roseomonas
Ruminococcus
Salibacillus
Salinibacillus
Salinicoccus
Schlegelella
Solirubrobacteraceae
Sphaerobacter
Spirochaeta
Staphylococcus
Steroidobacter
Streptococcus
Succiniclasticum
Symbiobacterium
Syntrophomonas
Tepidamorphus
Thermaerobacter
Thermanaeromonas
Thermoanaerobacter
Thermoanaerobacterium
Thermobacillus
Thermobifida
Thermoleophilum
Thermomicrobium
Thermus
Tissierella
unclassified_Incertae Sedis XI
unclassified_Thermaceae
Ureibacillus
Vagococcus
Virgibacillus
Vulcanithermus
Weissella Table 2 represents a list of genus names.

EXAMPLES

The present invention is described in more detail based on examples, but is not limited to these examples.

1. Production of Functional Microbial Materials

Functional microbial materials in Examples 1 and 2 were produced by the methods described below.

Example 1

For a fermentation raw material, a marine product-derived fermentation product was used which had been obtained by fermentation of a marine product including, as a plant-derived raw material, about 50% by weight of barley bran, about 20% by weight of, and about 10% by weight of rice bran, and further as an animal-derived raw material, about 20% by weight of crustaceans, such as shrimps and crabs, bottom fishes, and others caught by bottom trawling. The resulting marine product-derived fermentation product contained a population of microorganisms of from about $10^8$ cells/g to about $10^9$ cells/g, which was composed of about 70% to about 90% by weight of the microorganisms designated by the deposition number PTA-1773 and about 30% to about 10% by weight of the microorganisms designated by the deposition number NITE BP-1051.

The plant-derived raw material and the animal-derived raw material were mixed and well stirred, and then subjected to single-stage fermentation at 40° C. for 14 hours, followed by drying to obtain a functional culture feed according to the present invention. The resulting functional material contained a population of microorganisms of from about $10^8$ cells/g to about $10^9$ cells/g, which was composed of about 90% to about 99% by weight of the microorganisms designated by the deposition number PTA-1773 and about 10% to about 1% by weight of the microorganisms designated by the deposition number NITE BP-1051.

Example 2

For a fermentation raw material, a marine product was used which included, as a plant-derived raw material, about 20% by weight of a waste mushroom bed, and further as an animal-derived raw material, about 30% by weight of crustaceans, such as shrimps and crabs, bottom fishes, and others caught by bottom trawling. The waste mushroom bed contained a population of microorganisms of from about $10^8$ cells/g to about $10^9$ cells/g, which was composed of about 70% to about 90% by weight of the microorganisms designated by the deposition number PTA-1773 and about 30% to about 10% by weight of the microorganisms designated by the deposition number NITE BP-1051.

The plant-derived raw material and the animal-derived raw material were mixed and well stirred, and then subjected to two-stage fermentation. The fermentation conditions in the first stage were 50° C. to 60° C. and 4 hours to 5 hours, while the fermentation conditions in the second stage were 30° C. to 40° C. and 6 hours to 8 hours. After the second stage fermentation, the fermentation raw material that had gone through the fermentation process was dried to obtain a functional microbial material according to the present invention. The resulting functional microbial material contained a population of microorganisms of from about $10^8$ cells/g to about $10^9$ cells/g, which was composed of about 70% to about 90% by weight of the microorganisms designated by the deposition number PTA-1773 and about 30% to about 10% by weight of the microorganisms designated by the deposition number NITE BP-1051.

2. Activity for Degradation of Organic Substances in Soil and Water Environments with High Salt Concentration and High Alkalinity The populations of microorganisms designated as BP-1051 and as Thermophiles inoculum MIROKU M2K were cultured, for example, in a heart infusion medium with a salt concentration of 10%, to select bacteria species having an ability to degrade organic substances.

Strain IP-9, which is contained in the population of microorganisms designated as BP-1051, is a species closely related to the standard strain *Virgibacillus pantothenticus*, which produces ectoine, a component resistant to salt. Ectoine is known as a moisturizer. Actually, strain IP-9 was found to have an ability to degrade organic substances even at salt concentrations of 10% or higher. In addition, strain IP-9 is capable of co-culture with a species closely related to *Oceanobacillus profundus* which is contained in the flora of bacteria of multiple species. This species *Oceanobacillus profundus* is also known to have an ability to degrade organic substances at high salt and alkali concentrations; in fact, a species closely related to *Oceanobacillus profundus* was found as a species that was contained in the population of microorganisms designated as Thermophiles inoculum MIROKU M2K. At present, it has not become possible to perform persistent culturing of these bacteria species as an isolated strain. In any case, it can be said that functions of these bacteria species contribute to the cleanup of soil and water environments with high salt concentration and high strong alkali concentration.

3. Evaluation of Decreasing Nitrate for Soils, Plant Bodies, and Others

*Arabidopsis thaliana* was used as a model plant, and experiments were carried out in KUREHA culture soil (surface soil of a depth of 5 cm) as a nutrient soil. In brief, after vernalization treatment was applied overnight at 4° C., cultivation was carried out for 21 days in a temperature-controlled room (at 23° C.) under 24-hour light conditions at an illuminance of 10,000 lux, with 100 ml of water being added every other day.

A graph showing the effect of decreasing nitrate in the plant is given in FIG. 3. A graph showing the effect of decreasing nitrate in the soil is given in FIG. 4. As shown in FIGS. 3 and 4, it was ascertained that the concentration of nitrate within the plant body and in the soil was reduced in a manner dependent on the concentration of the added material according to the present invention. It can be said that as shown in FIGS. 5 and 6, the nitrate in these cases does not penetrate into the ground, but is denitrified, and thus causes no pollution. This tendency was also observed for the hydrosphere; there was found the effect of reducing the concentrations of nitrate ions, ammonium ions, and total nitrogen in water during wastewater treatment.

6. Induction of Lateral Roots and Expression of Nitrate Transporters

For *Brassica rapa* var. *perviridis*, which is referred to in Japan as komatsuna, black earth and red soil were mixed at a ratio of 8:2 to prepare 300 g of an experimental soil. To this soil, 200 ml of water was add, and then the soil was covered with aluminum foil and left to stand at a cold dark place for 1 week. The soil was then transferred into a room into which natural light came and sown with seeds, and after that 100 ml of water was added. Since then, water was added every two days. For *Arabidopsis thaliana*, which was used as a model plant, experiments were carried out in KUREHA culture soil as a nutrient soil. As mentioned above, after vernalization treatment was applied overnight at 4° C., cultivation was carried out for 21 days in a temperature-controlled room (at 23° C.) under 24-hour light conditions at an illuminance of 10,000 lux, with a certain amount of water being added so that the soil did not become dry.

As shown in FIG. 5, the experiments using *Brassica rapa* var. *perviridis* resulted in a 20% or more increase in generated roots. This tendency was also observed in any of leaf vegetables, root crops, fruit vegetables, and fruit trees.

Next, *Arabidopsis thaliana* was used as a model plant, and experiments were carried out in KUREHA culture soil (surface soil of a depth of less than 3 cm) as a nutrient soil. In brief, after vernalization treatment was applied for 48 hours at 4° C., cultivation was carried out for 21 days in a temperature-controlled room (at 23° C.) under 24-hour light conditions at an illuminance of 10,000 lux, with retaining a certain amount of water.

TABLE 3

Genes highly expressed in *Arabidopsis thaliana* - part 1: claim 6

| Genbank | Common Description | Regulation |
|---|---|---|
| At5g52640/At1g74310 At5g02490/At3g09440 | Heat shock protein family | up |
| At4g15440 | HPL1 (HYDROPEROXIDE LYASE 1) | up |

TABLE 3-continued

Genes highly expressed in *Arabidopsis thaliana* - part 1: claim 6

| Genbank | Common Description | Regulation |
| --- | --- | --- |
| At5g59320/At3g22600 | LTP (LIPID TRANSFER PROTEIN) related protein | up |
| At1g52770 | Phototropic-responsive NPH3 family protein | up |
| At1g73325 | trypsin and protease inhibitor family protein/Kunitz family protein | up |
| At2g17500 | Auxin efflux carrier family protein | up |
| At2g04240/At5g17600 | RING-H2 gene, XERICO | up |

TABLE 4

Genes highly expressed in *Arabidopsis thaliana* - part 2: claim 6

| Genbank | Common Description | Regulation |
| --- | --- | --- |
| AF325030 | Glutaredoxin family protein | up |
| AK176211/BT012184 | Glutathione S-transferase | up |
| At5g02490/AY128296 AY054183/At5g02490 | Heat shock protein related family | up |
| AY087779 | Oxidoreductase | up |
| AF419593 | Nodulin family protein | up |
| AY078973 | Senescence-associated protein (SEN1) | up |
| AY057661 | SOUL heme-binding family protein | up |
| AF386952 | Ras-related GTP-binding family protein | up |
| AK118884/AF426252 AY091154/AY088908 | WRKY family transcription factor | up |
| AK117967 | Cytochrome P450 71B15, putative | up |
| AF426253 | Aspartyl protease family protein | up |

Table 3 indicates a group of genes that are highly expressed by means of the functional material according to the present invention when *Arabidopsis thaliana* is cultivated using the soil of a depth of 5 cm. Table 4 indicates a group of genes that are highly expressed by means of the functional material according to the present invention when *Arabidopsis thaliana* is cultivated using the soil of a depth of less than 3 cm.

mRNAs in root and stem parts were extracted and analyzed by RT-PCR. From the results, it was found that the amount of expression of NRT2.1, a nitrate transporter, tended to be increased 2 times or more (FIG. 6). It was also found that the expression of NRT2.6 tended to be increased. Further, as shown in Table 3, it can be said that the amount of expression of genes related to auxin is significantly increased. Further, as shown in Table 4, it would also be important that a nodulin like protein is expressed. Recently, it has been suggested that nodulin contributes to the formation of roots by flagellin, which is an extracellular component (Planta 234: 459-476, 2011).

As described above, the functional material according to the present invention brings about promotion and induction of rooting, as well as has an effect of enhancing the expression of nitrate transporter and auxin-related genes in root hairs. In addition, it is supposed that the functional material according to the present invention gives rise to an increase in photoresponsiveness, because as shown in Table 3, a phototropism regulating gene, which encodes a phototropic-responsive NPH3 family protein, is also strongly expressed. These combined factors would allow plants to efficiently absorb nutrients in the soil even when the soil contains small amounts of fertilizer components and make it possible to promote the growth of plants. Effects of promoting the growth of plants involve not only functions of these genes, but also a species closely related to *Bacillus graminis* which is difficult to culture and is a bacteria species that is contained in the population of microorganisms designated as Thermophiles inoculum MIROKU M2K. *Bacillus graminis* is a microbial endophyte living in symbiosis with plants, and thus is supposed to be likely to contribute to the promotion of the growth of the plants.

3. Evaluation of the Ability to Inhibit the Generation of a Greenhouse Gas, Dinitrogen Monoxide

*Arabidopsis thaliana* was used as a model plant, and experiments were carried out in KUREHA culture soil (surface soil of a depth of 5 cm) as a nutrient soil. In brief, after vernalization treatment was applied overnight at 4° C., cultivation was carried out for 21 days in a temperature-controlled room (at 23° C.) under 24-hour light conditions at an illuminance of 10,000 lux, with 100 ml of water being added every other day.

As shown in FIG. 6, also under an atmosphere containing acetylene, the soil to which the material according to the present invention had been added resulted in a great decrease in the concentration of nitrate ions in the soil, whereas the soil with no addition was difficult to decrease the concentration of nitrate ions in the soil. Since acetylene inhibits the reaction from $N_2O$ to $N_2$, its inhibitory reaction can be used to detect $N_2O$ by gas chromatography. Accordingly, in the case of a soil where $N_2O$ is generated, $N_2O$ will be detected also under an atmosphere in which acetylene is not mixed; in the case of a soil where $N_2$ is generated, $N_2O$ can be detected only under an atmosphere in which acetylene is mixed. As shown in FIG. 7, the soil to which the material according to the present invention had been added did not allow the detection of $N_2O$ under conditions of the soil that had not been subjected to acetylene blockage. On the other hand, the soil that had been subjected to acetylene blockage allowed $N_2O$ to be detected. Therefore, it turned out that this soil had a property of preferentially emitting $N_2$. From these, it can be said that nitrate ions in the soil are denitrified as $N_2$ gas.

To search genes that promote these reactions, PCR detection of such genes was performed, for example, by reference to primer sequences described in Throback I N et al. (2004) Reassessing PCR primers targeting nirS, nirK and nosZ genes for community surveys of denitrifying bacteria with DGGE. FEMS Microbiol. Ecol. 49:401-417, which was used as a reference. The primers for NirK used the sequences of 5'-GGCGGCGCGCCGCCCG-CCCCGCCCCCGTCGCCCGCCTCGATCAGATTGTG GTT-3' as a forward primer and 5'-AT-CATGGTCCTGCCGCG-3' as a reverse primer. The primers for NirS used the sequences of 5'-GGCGGCGCGCCGCCCGCCCCGCCCCCGTC-GCCCGACTTCGGATGCGTCTT GA-3' as a forward primer and 5'-GTCAACGTCAAGGAAACCGG-3' as a reverse primer. The primers for NosZ used, for example, the sequences of 5'-TGGGGNGAYNTBCAYCA-3' as a forward primer and 5'-GARCARAAGTTIGTRCARTA-3' as a reverse primer. References used were Scala D J and Kerkhof L J (1998) Nitrous oxide reductase (nosZ) gene-specific PCR primers for detection of denitrifiers and three nosZ genes from marine sediments. FEMS Microbiology Letters 162:61-68; and Jones, C. M., Welsh, A., Throbäck, I. N., Dörsch, P., Bakken L. R., Hallin, S. (2011) Phenotypic and genotypic heterogeneity among closely related soil-borne $N_2$- and $N_2O$-producing *Bacillus* isolates harboring the nosZ gene. FEMS Microbiol. Ecol. 76: 541-552. PCR results revealed that it was likely that genes of which the sequences are closely related to gene sequences encoding denitrification enzymes derived from the genus *Bradyhizobium*, *Herbaspirillum*, and *Mesorhizobium* work.

TABLE 5

Comparison of sequence homologies between denitrification genes derived from the material according to the present invention

| No. | deposit no. | Closely related species | Identity (%) |
|---|---|---|---|
| S-1 | AB686171 | *Bradyhizobium* sp. TSA44 | 84 |
| S-2 | AB686172 | *Herbaspirillum* sp. TSO20-1 | 96 |
| S-3 | AB686170 | *Mesorhizobium* sp. TSA41b | 97 |

Table 5 indicates the homology between denitrification-associated genes included in the functional material according to the present invention and denitrification genes in some standard strains.

4. Evaluation of Nitrogen Fixation

*Arabidopsis thaliana* was used as a model plant, and experiments were carried out in KUREHA culture soil (surface soil of a depth of 5 cm) as a nutrient soil. In brief, after vernalization treatment was applied overnight at 4° C., cultivation was carried out for 21 days in a temperature-controlled room (at 23° C.) under 24-hour light conditions at an illuminance of 10,000 lux, with 100 ml of water being added every other day. The degree of dryness of the soil (decrease in the water content) was regulated by extending the time interval of addition of water by a few days.

As shown in FIG. 8, the concentration of ammonium ions within the body of *Arabidopsis thaliana* tended to increase. Since the concentration of nitrate within the body of plants is extremely low and the activity of nitrate reducing enzymes is low, it is expected that the ammonium ions are from sources other than nitrate and are produced by microorganisms. In this connection, nitrogen fixation by microorganisms is known to be catalyzed by a nitrogenase complex, which includes dinitrogenase and dinitrogenase reductase as its factors. Further, the dinitrogenase reductase is reduced by electron donors such as ferredoxin and flavodoxin, resulting in the formation of ammonium ions.

Based on these, primers capable of amplification of nifH, which is a gene for dinitrogenase reductase, were used to investigate the cause for increased ammonium ions. The primers for nifH used, for example, the sequences of 5'-TGCGACCCGAAAGCCGACTC-3' as a forward primer and 5'-ATGGCCATCATCTCACCGGA-3' as a reverse primer, to search for the nifH gene, by reference to Widmer F, Shaffer B T, Porteous L A and Seidler R J (1999) Analysis of nifH Gene Pool Complexity in Soil and Litter at a Douglas Fir Forest Site in the Oregon Cascade Mountain Range. Appl Environ Microbiol 65: 374-380, and Poly, F., Monrozier, L. J., Bally, R. (2001) Improvement in the RFLP procedure for studying the diversity of nifH genes in communities of nitrogen fixers in soil. Res. Microbiol. 152: 95-103.

Out of the bacteria contained in the material according to the present invention, bacteria species were isolated which were capable of growing in a nitrogen-free medium containing succinic acid serving as an electron donor. As a result, among these bacteria species were species of the genera *Lysinibacillus* and *Peanibacillus*, which are species closely related to IP-23, and IP-60 and 75 contained in the population of microorganisms designated as NITE BP-1051. Further, as shown in Tables 6 and 7, there were included *Bacillus* sp. strain 36W, which is a species closely related to *Bacillus pumilus* and *Bacillus safensis*, and *Brevibacillus* sp. strain 123, which is a species closely related to *Brevibacillus choshinensis* and *B. brevis*, judging from the results of BLAST analysis of 16S rDNA sequences. Although the latter was identifiable using the above-described primers, strains that cannot be identified using these primers were also included. For any of these strains, its base sequence was not completely identical to that of the standard strain, and the strain was considered to be a new species or subspecies. It was also suggested that these strains exhibited their ability for nitrogen fixation in a synergistic way as a form of a population of bacteria of multiple species. In this connection, the population of microorganisms designated as NP-1051 includes a species closely related to *Bacillus badius*, which is known to have a group of genes involved in the metabolism of nitrogen and is expected to play some role by its co-existence. In addition, as shown in Table 3, the amount of expression of Senescence-associated protein (SEN1) is increased in plants that have been grown in the soil having the material according to the present invention added thereto, and it is interesting that it has recently been reported that SEN1 is a factor necessary to nitrogen fixation bacteria living in symbiosis with plants (Plant Cell Physiol 2011, in press, http://pcp.oxfordjournals.org/content/early/2011/11/28/pcp.per167.long).

Further, *Paenibacillus* sp. that is a functional microorganism in the high-temperature fermentation product has an ability to live in symbiosis with plants as a plant-symbiotic bacterium. *Paenibacillus* sp. is included in the population of microorganisms designated as NITE BP-1051 that has been internationally deposited. For these thermophilic, plant-symbiotic bacteria, their base sequences of 16S rRNA were determined to construct a phylogenetic tree. As shown in FIG. 12, *Paenibacillus* sp. is similar to *Paenibacillus amylolyticus* and *Paenibacillus barcinonensis* and was found to be a thermophilic bacterium capable of growing also at 50° C. Plants to which the high-temperature fermentation product has been applied have these strains living in symbiosis therewith, and therefore it is supposed that the promotion of the expression of genes related to the promotion and regulation of the growth of plants and to the biophylaxis of plants, and effects against plant damages by nematodes as small organisms involve *Paenibacillus* sp. contained in the population of microorganisms designated as BP-1051 and in the fermentation product.

TABLE 6

A nitrogen fixation bacterium included in the population of microorganisms designated as *Thermophiles inoculum* MIROKU M2K: claim 7 *Bacillus* sp 36W strain (a species closely related to *Bacillus pumilus* and *Bacillus safensis*)

GACAGAAGGGAGCTTGCTCCCGGATGTTAGCGGCGGACGGGTGAGTAACA

CGTGGGTAACCTGCCTGTAAGACTGGGATAACTCCGGGAAACCGGAGCTA

ATACCGGATAGTTCCTTGAACCGCATGGTTCAAGGATGAAAGACGGTTTC

GGCTGTCACTTACAGATGGACCCGCGGCGCATTAGCTAGTTGGTGGGGTA

ATGGCTCACCAAGGCGACGATGCGTAGCCGACCTGAGAGGGTGATCGGCC

ACACTGGGACTGAGACACGGCCCAGACTCCTACGGGAGGCAGCAGTAGGG

AATCTTCCGCAATGGACGAAAGTCTGACGGAGCAACGCCGCGTGAGTGAT

GAAGGTTTTCGGATCGTAAAGCTCTGTTGTTAGGGAAGAACAAGTGCGAG

AGTAACTGCTCGCACCTTGACGGTACCTAACCAGAAAGCCACGGCTAACT

TABLE 6-continued

A nitrogen fixation bacterium included in the
population of microorganisms designated as
Thermophiles inoculum MIROKU M2K: claim 7
Bacillus sp 36W strain
(a species closely related to
Bacillus pumilus and Bacillus safensis)

ACGTGCCAGCAGCCGCGGTAATACGTAGGTGGCAAGCGTTGTCCGGAATT

ATTGGGCGTAAAGGGCTCGCAGGCGGTTTCTTAAGTCTGATGTGAAAGCC

CCCGGCTCAACCGGGGAGGGTCATTGGAAACTGGGAAACTTGAGTGCAGA

AGAGGAGAGTGGAATTCCACGTGTAGCGGTGAAATGCGTAGAGATGTGGA

GGAACACCAGTGGCGAAGGCGACTCTCTGGTCTGTAACTGACGCTGAGGA

GCGAAAGCGTGGGGAGCGAACAGGATTAGATACCCTGGTAGTCCACGCCG

TAAACGATGAGTGCTAGTGTTAGGGGTTTCCGCCCCTTAGTGCTGCAGCT

AACGCATTAAGCACTCCGCCTGGGGAGTACGGTCGCAAGACTGAAACTCA

AAGGAATTGACGGGGGCCCGCACAAGCGGTGGAGCATGTGGTTTAATTCG

AAGCAACGCGAAGAACCTTACCAGGTCTTGACATCCTCTGACAACCCTAG

AGATAGGGCYPTCCCTTCGGGGACAGAGTGACAGGTGGTGCATGGTTGTC

GTCAGCTCGTGTCGTGAGATGTTGGGTTAAGTCCCGCAACGAGCGCAACC

CTTGATCTTAGTTGCCAGCATTCAGTTGGGCACTCTAAGGTGACTGCCGG

TGACAAACCGGAGGAAGGTGGGGATGACGTCAAATCATCATGCCCCTTAT

GACCTGGGCTACACACGTGCTACAATGGACAGAACAAAGGGCTGCAAGAC

CGCAAGGTTTAGCCAATCCCATAAATCTGTTCTCAGTTCGGATCGCAGTC

TGCAACTCGACTGCGTGAAGCTGGAATCGCTAGTAATCGCGGATCAGCAT

GCCGCGGTGAATACGTTCCCGGGCCTTGTACACACCGCCCGTCACACCAC

GAGAGTTTGCAACACCCGAAGTCGGTGAGGTAACCTTTATGGAGCCAGCC

GCCGAAGGTGGGGCAGATGATTGGGGTGAAGTCGTACAAAGGTAGCCCA

TABLE 7

A nitrogen fixation bacterium included in the
population of microorganisms designated as
Thermophiles inoculum MIROKU M2K: claim 7
Brevibacillus sp 123 strain
(a species closely related to Brevibacillus
choshinensis and Brevibacillus brevis)

CTGCCGGCGTGCCTATACTGCAAGTCGAGCGAGTCTCTTCGGAGGCTAGC

GGCGGACGGGTGAGTAACACGTAGGCAACCTGCCTCTCAGACTGGGATAA

CATAGGGAAACTTATGCTAATACCGGATAGGTTTTTGGATCGCATGATCC

AAAAAGAAAAGGCGGCTTTAAGCTGTCACTGGGAGATGGGCCTGCGGCGC

ATTACCTAGTTGGTGGGGTAATGGCCTACCAAGGCGACAATGCGTACCCG

ACCTGAAAGGGTGACCGGCCACACTGGGACTGAAACACGGCCCAAACTCC

TACGGGAGGCAGCAGTAGGGAATTTTCCACAATGGACGAAAGTCTGATGG

AGCAACGCCGCGTGAACGATGAAGGTCTTCGGATTGTAAAGTTCTGTTGT

TAGGGACAAACAAGTACCGTTCGAATAGGGCGGTACCTTGACGGTACCTG

ACGAGAAAGCCACGGCTAACTACGTGCCACCAGCCGCGGTAATACGTAGG

TABLE 7-continued

A nitrogen fixation bacterium included in the
population of microorganisms designated as
Thermophiles inoculum MIROKU M2K: claim 7
Brevibacillus sp 123 strain
(a species closely related to Brevibacillus
choshinensis and Brevibacillus brevis)

TGGCAAGCGTTGTCCGGATTTATTGGGCGTAAAGCGCGCGCAGGCGGCTA

TGTAAGTCTGGTGTTAAAGCCCGGAGCTCAACTCCGGTTCGCATCGGAAA

CTGTGTAGCTTGAGTGCAAAAGAGGAAAGCGGTATTCCACGTGTAGCGGT

GAAATGCGTAGAGATGTGGAGGAACACCAGTGGCGAAGGCGGCTTTCTGG

TCTGTAACTGACGCTGAGGCGCGAAAGCTGTGGTGGAGCAAACAGGATTA

GATACCCTGCTAGTCCACGCCGTAAACGATGAGTGCTAGGTGTTGGGGTT

TCATACCTCAATTGCCGCAG

Table 6 shows the sequence of 16S rDNA from a nitrogen fixation bacterium *Bacillus* sp strain 36W that is contained in the functional material according to the present invention. Table 7 shows the sequence of 16S rDNA from a nitrogen fixation bacterium *Brevibacillus* sp strain 123 that is contained in the functional material according to the present invention.

7. Evaluation of Functions of Regulating Amino Acid Concentrations

*Arabidopsis thaliana* was used as a model plant, and experiments were carried out in KUREHA culture soil (surface soil of a depth of 5 cm) as a nutrient soil. In brief, after vernalization treatment was applied overnight at 4° C., cultivation was carried out for 21 days in a temperature-controlled room (at 23° C.) under 24-hour light conditions at an illuminance of 10,000 lux, with 100 ml of water being added every other day. The degree of dryness of the soil (decrease in the water content) was regulated by extending the time interval of addition of water by a few days.

As shown in FIG. 10, the concentrations of glutamic acid and glutamine within the body of *Arabidopsis thaliana* were significantly increased in the group in which the material according to the present invention had been added to the soil. There was observed the tendency that arginine, which is subjected to degradation into glutamic acid, was remarkably increased. Glutamic acid is produced from an ammonium ion, and therefore it also turned out that the result shown in FIG. 9 is not inconsistent with those in FIG. 10. In general, plant-derived glutamic acid not only is involved in the taste of crops, but also is an amino acid of critical importance, for example, in the expression of every anti-oxidation enzyme. Therefore, it can be said that the material according to the present invention contributes to the quality of plants and an improvement in their functionality. In this connection, nodulin, a strongly expressed gene in Table 4, is also known to contribute to the glutamine synthesis function (Planta 234: 459-476, 2011), and is not inconsistent with the results from examples according to the present invention.

When the content of water in the cultivation soil decreased by 10%, there was observed the tendency that proline was remarkably increased in the group in which the material according to the present invention had been added to the soil, as shown in FIG. 11. Proline within the body of plants is produced from glutamic acid, for example, by the reaction with P5C reductase (Pyrroline-5-carboxylate reductase) and is transformed as glutamic acid, for example, by the reaction with Prolin oxidase, during dryness, whereas the expression of prolin oxidase is increased by 2 times or more under high water content conditions. Therefore, the result for proline shown in FIG. 11 had no inconsistency in the relation with the concentration of glutamic acid. In this connection, it is generally known that proline is an amino acid involved in resistance to dryness and moisture retention, and the like. Therefore, it can be said that the material according to the present invention contributes to an improvement in the functionality of plants also from these points of view.

8. Expression of Genes Resistant to High-Temperature Disorder and Disease-Resistant Responsive Genes Since a plant growing environment varies in the nature, a model plant *Arabidopsis thaliana* was cultivated under different cultivation conditions to analyze the pattern of expressed gene. *Arabidopsis thaliana* was used as a model plant, and experiments were carried out in KUREHA culture soil as a nutrient soil. Table 3 indicates the results obtained from experiments that had been carried out using a surface soil of a depth of 5 cm. After vernalization treatment was applied overnight at 4° C., cultivation was carried out for 21 days in a temperature-controlled room (at 23° C.) under 24-hour light conditions at an illuminance of 10,000 lux, with 100 ml of water being added every other day. Table 4 indicates the results obtained from experiments that had been carried out using a surface soil of a depth of less than 3 cm. After vernalization treatment was applied overnight at 4° C., cultivation was carried out for 21 days in a temperature-controlled room (at 23° C.) under 24-hour light conditions at an illuminance of 10,000 lux, with a certain amount of water being added so that the soil did not become dry. Under these conditions, DNA microarray analysis (a method similar to that described in the previous PCT application) was carried out for global screening of genes strongly expressed in the model plant.

Tables 3 and 4 show a group of genes ubiquitously and strongly expressed in *Arabidopsis thaliana* that was grown in the soil to which the material according to the present invention had been added. Especially, the expression of Heat shock proteins (HSPs), which are molecular chaperones, was observed. Regarding HSPs, the amounts of expression of the HSP70 family, HSP90 family, HSP101 family, and others were increased.

Regarding HSPs among the genes of which the amounts of expression vary, any of the HSPs is a factor contributing to resistance functions against high-temperature stress and various environmental stresses (Trends Plant Sci 9: 244-252, 2004; Science 330: 1820-1824, 2010; Plant Cell, Vol. 12, 457-460, 2000). Furthermore, the RING-H2 gene, XERICO, is involved in the regulation of the generation of an important plant hormone, abscisic acid, that works in controlling the growth, and dryness resistance, salt resistance, and others, of plants (Plant Journal 47: 343-355, 2006).

Regarding dryness resistance, it is interesting that as shown in FIG. 11, the degree of the increase in the proline concentration was varied when the cultivation was performed in the soil to which the material according to the present invention had been added and then transferred into conditions where the content of water in the soil decreased by 10%.

Further, as factors involved in biophylaxis, HSP70 and HSP90 as HSPs are known to contribute to disease-resistant functions together with SGT1 and RAR1 (Plant Cell 19: 4061-4076, 2007; J Biol Chem 279: 2101-2108, 2004; EMBO J 27:2789-2798, 2008). Nodulin is also known to be a gene involved in disease-resistant properties (Olivares J E et al. (2011) Nodulin 41, a novel late nodulin of common bean with peptidase activity. BMC Plant Biol 10:134). The expression of Senescence-associated protein (SEN1) is regulated by salicylic acid and jasmonic acid signaling, and SEN1 is supposed to be a marker gene related to disease-resistant properties. In this connection, salicylic acid is a factor involved in resistance to various pathogenic microorganisms such as viruses and bacteria; jasmonic acid acts antagonistically with salicylic acid, and on the other hand, is known to be a factor inducing resistance to environmental stresses.

As a pathogen-resistance gene, an LTP (LIPID TRANSFER PROTEIN) (Nature 419: 399-403, 2002) is strongly expressed. Trypsin and protease inhibitor/Kunitz family protein is known to be a gene exhibiting resistance to various pathogens (Molecular Plant 1: 482-495, 2008), and is an antagonist that antagonizes cell death induced by a mycotoxin, fumonisin B1. Further, HPL1 (HYDROPEROXIDE LYASE 1) is a factor that is known to stop activities of aphids (Proc Natl Acad Sci USA 98: 8139-8144, 2001), and was found to result in strong expression of Cytochrome P450 71B15, putative (CYP71B15), that biosynthesizes phytoalexins. P450 71B15 is a cytochrome enzyme that is known to produce the phytoalexin Camalexin (Plant Cell 8: 2235-2244, 1996). Camalexin is known to inhibit the propagation of pathogenic filamentous fungi and bacteria. Since these enzymes are induced by environmental stresses and elicitors (Plant Cell 10: 359-370, 1998), it is supposed that the material according to the present invention brings about changes in the soil environment and functions as an elicitor.

Further, even once plants are infected with pathogens, aspartyl protease, which is known to prevent cell death within the plant body (EMBO J. 2004 Feb. 25; 23(4): 980-988; EMBO reports 6: 282-288), can also be strongly expressed.

As mentioned above, the expression of many biophylaxis-related genes is induced; it can be said that there is no inconsistency with strong expression of WRKY family transcription factors, which are known to be genes that can be involved in the regulation of the transcription of these genes (Plant Mol Biol, 51: 21-37, 2003). Further, Glutaredoxin family protein and Glutathione S-transferase, which are shown in Table 4, are involved in antioxidation activities and at the same time, have a tendency to also increase vitamins C and E, and therefore it can be said that the antioxidation activity within the plant body is improved.

The populations of microorganisms designated as PTA-1773 and as Thermophiles-inoculum M2K (of which the deposition was not accepted) that are used for stabilizing the material according to the present invention, which contain chitin-degrading enzymes and highly antifungally active lipopeptides, can primarily decrease the presence ratio of filamentous fungi in the soil and plant body, or in the hydrosphere when the material according to the present invention has been applied to a test field.

Therefore, when the material according to the present invention has been used in the field of agriculture, environmental control can be achieved from both outside and inside the plant body because the material decreases the presence ratio of pathogenic filamentous fungi as a growth environment outside the plant body, while activating biophylaxis-related genes inside the plant body.

Deposition Numbers
 ATCC PTA-1773
 NITE BP-1051

Sequence Listing

The invention claimed is:

1. A method for inducing expression of a functional component resistant to high-temperature disorder, dryness resistance, antioxidation activity, plant pathogenic microorganisms and insect pests in a plant by administering a fermented material comprising PTA-1773 and BP-1051 to said plant.

2. The method according to claim 1, wherein the fermented material is obtained by following steps comprising:
a stirring step of stirring 50% to 90% by weight of a plant-derived raw material and 50% to 10% by weight of an animal-derived raw material to obtain a fermentation raw material; and
a fermentation step of subjecting the fermentation raw material obtained by the stirring step to fermentation using microorganisms comprising BP-1051 and PTA-1773 with a temperature of 20° C. to 90° C. for about 5 to about 24 hours.

3. The method according to claim 2, wherein a population of the microorganisms used in the fermentation step is composed of about 70% to about 90% by weight of PTA-1773 and about 30% to about 10% by weight of BP-1051.

4. A method for promoting induction of lateral roots and activity of expression of nitrate transporters in a plant by administering the fermented material recited in claim 1 to said plant.

5. The method according to claim 1, wherein the plant-derived raw material comprises one or more selected from the group consisting of rice bran, barley bran, broken husks, soybean cake, bean curd refuse, sake lees, distilled spirit lees, tea leaves residuals, coffee grounds, residues after squeezing fruits, and residues after squeezing vegetables.

6. The method according to claim 5, wherein the animal-derived raw material comprises one or more selected from the group consisting of crustaceans, fishes, residues after processing crustaceans, and residues after processing fishes.

7. The method according to claim 1, wherein the animal-derived raw material comprises one or more selected from the group consisting of crustaceans, fishes, residues after processing crustaceans, and residues after processing fishes.

8. The method according to claim 4, wherein the fermented material is obtained by following steps comprising:
a stirring step of stirring 50% to 90% by weight of a plant-derived raw material and 50% to 10% by weight of an animal-derived raw material to obtain a fermentation raw material; and a fermentation step of subjecting the fermentation raw material obtained by the stirring step to fermentation using microorganisms comprising BP-1051 and PTA-1773 with a temperature of 20° C. to 90° C. for about 5 to about 24 hours.

9. The method according to claim 8, wherein a population of the microorganisms used in the fermentation step is composed of about 70% to about 90% by weight of PTA-1773 and about 30% to about 10% by weight of BP-1051.

10. The method according to claim 4, wherein the plant-derived raw material comprises one or more selected from the group consisting of rice bran, barley bran, broken husks, soybean cake, bean curd refuse, sake lees, distilled spirit lees, tea leaves residuals, coffee grounds, residues after squeezing fruits, and residues after squeezing vegetables.

11. The method according to claim 10, wherein the animal-derived raw material comprises one or more selected from the group consisting of crustaceans, fishes, residues after processing crustaceans, and residues after processing fishes.

12. The method according to claim 4, wherein the animal-derived raw material comprises one or more selected from the group consisting of crustaceans, fishes, residues after processing crustaceans, and residues after processing fishes.

* * * * *

```
                              SEQUENCE LISTING

<160> NUMBER OF SEQ ID NOS: 10

<210> SEQ ID NO 1
<211> LENGTH: 53
<212> TYPE: DNA
<213> ORGANISM: Artificial Sequence
<220> FEATURE:
<223> OTHER INFORMATION: Forward primer to detect NirK mRNA

<400> SEQUENCE: 1
ggcggcgcgc cgcccgcccc gccccgtcg cccgcctcga tcagattgtg gtt            53

<210> SEQ ID NO 2
<211> LENGTH: 17
<212> TYPE: DNA
<213> ORGANISM: Artificial Sequence
<220> FEATURE:
<223> OTHER INFORMATION: Reverse primer to detect NirK mRNA

<400> SEQUENCE: 2
atcatggtcc tgccgcg                                                   17

<210> SEQ ID NO 3
<211> LENGTH: 52
<212> TYPE: DNA
<213> ORGANISM: Artificial Sequence
<220> FEATURE:
<223> OTHER INFORMATION: Forward primer to detect NirS mRNA

<400> SEQUENCE: 3
ggcggcgcgc cgcccgcccc gccccgtcg cccgacttcg gatgcgtctt ga             52

<210> SEQ ID NO 4
<211> LENGTH: 20
<212> TYPE: DNA
<213> ORGANISM: Artificial Sequence
<220> FEATURE:
<223> OTHER INFORMATION: Reverse primer to detect NirS mRNA

<400> SEQUENCE: 4
gtcaacgtca aggaaaccgg                                                20

<210> SEQ ID NO 5
<211> LENGTH: 17
<212> TYPE: DNA
<213> ORGANISM: Artificial Sequence
<220> FEATURE:
<223> OTHER INFORMATION: Forward primer to detect NosZ mRNA
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t

<400> SEQUENCE: 5
tggggngayn tbcayca                                                   17

<210> SEQ ID NO 6
<211> LENGTH: 19
<212> TYPE: DNA
<213> ORGANISM: Artificial Sequence
<220> FEATURE:
<223> OTHER INFORMATION: Reverse primer to detect NosZ mRNA
```

<400> SEQUENCE: 6
garcaraagt tgtrcarta                                                                 19

<210> SEQ ID NO 7
<211> LENGTH: 20
<212> TYPE: DNA
<213> ORGANISM: Artificial Sequence
<220> FEATURE:
<223> OTHER INFORMATION: Forward primer to detect NifH mRNA

<400> SEQUENCE: 7
tgcgacccga aagccgactc                                                                20

<210> SEQ ID NO 8
<211> LENGTH: 20
<212> TYPE: DNA
<213> ORGANISM: Artificial Sequence
<220> FEATURE:
<223> OTHER INFORMATION: Reverse primer to detect NifH mRNA

<400> SEQUENCE: 8
atggccatca tctcaccgga                                                                20

<210> SEQ ID NO 9
<211> LENGTH: 1449
<212> TYPE: DNA
<213> ORGANISM: Unknown
<220> FEATURE:
<223> OTHER INFORMATION: Related species of Bacillus pumilus or
      Bacillus safensis

<400> SEQUENCE: 9
gacagaaggg agcttgctcc cggatgttag cggcggacgg gtgagtaaca cgtgggtaac         60
ctgcctgtaa gactgggata actccgggaa accggagcta ataccggata gttccttgaa        120
ccgcatggtt caaggatgaa agacggtttc ggctgtcact tacagatgga cccgcggcgc        180
attagctagt tggtgggta atggctcacc aaggcgacga tgcgtagccg acctgagagg        240
gtgatcggcc acactgggac tgagacacgg cccagactcc tacgggaggc agcagtaggg        300
aatcttccgc aatggacgaa agtctgacgg agcaacgccg cgtgagtgat gaaggttttc        360
ggatcgtaaa gctctgttgt tagggaagaa caagtgcgag agtaactgct cgcaccttga        420
cggtacctaa ccagaaagcc acggctaact acgtgccagc agccgcggta atacgtaggt        480
ggcaagcgtt gtccggaatt attgggcgta aagggctcgc aggcggtttc ttaagtctga        540
tgtgaaagcc cccggctcaa ccggggaggg tcattggaaa ctgggaaact tgagtgcaga        600
agaggagagt ggaattccac gtgtagcggt gaaatgcgta gagatgtgga ggaacaccag        660
tggcgaaggc gactctctgg tctgtaactg acgctgagga gcgaaagcgt ggggagcgaa        720
caggattaga taccctggta gtccacgccg taaacgatga gtgctagtgt taggggtttc        780
cgccccttag tgctgcagct aacgcattaa gcactccgcc tggggagtac ggtcgcaaga        840
ctgaaactca aaggaattga cggggcccg cacaagcggt ggagcatgtg gtttaattcg        900
aagcaacgcg aagaaccttac caggtcttg acatcctctg acaaccctag atatagggct        960
ttcccttcgg ggacagagtg acaggtggtg catggttgtc gtcagctcgt gtcgtgagat       1020
gttgggttaa gtcccgcaac gagcgcaacc cttgatctta gttgccagca ttcagttggg       1080
cactctaagg tgactgccgg tgacaaaccg gaggaaggtg gggatgacgt caaatcatca       1140
tgccccttat gacctgggct acacacgtgc tacaatggac agaacaaagg gctgcaagac       1200

```
cgcaaggttt agccaatccc ataaatctgt tctcagttcg gatcgcagtc tgcaactcga    1260
ctgcgtgaag ctggaatcgc tagtaatcgc ggatcagcat gccgcggtga atacgttccc    1320
gggccttgta cacaccgccc gtcacaccac gagagtttgc aacacccgaa gtcggtgagg    1380
taacctttat ggagccagcc gccgaaggtg gggcagatga ttggggtgaa gtcgtacaaa    1440
ggtagccca                                                           1449

<210> SEQ ID NO 10
<211> LENGTH: 820
<212> TYPE: DNA
<213> ORGANISM: Unknown
<220> FEATURE:
<223> OTHER INFORMATION: Related species of  Brevibacillus choshinensis
      or Brevibacillus brevis

<400> SEQUENCE: 10
ctgccggcgt gcctatactg caagtcgagc gagtctcttc ggaggctagc ggcggacggg      60
tgagtaacac gtaggcaacc tgcctctcag actgggataa catagggaaa cttatgctaa     120
taccggatag gttttggat cgcatgatcc aaaagaaaa ggcggcttta agctgtcact       180
gggagatggg cctgcggcgc attacctagt tggtggggta atggcctacc aaggcgacaa     240
tgcgtacccg acctgaaagg gtgaccggcc acactgggac tgaaacacgg cccaaactcc     300
tacgggaggc agcagtaggg aattttccac aatggacgaa agtctgatgg agcaacgccg     360
cgtgaacgat gaaggtcttc ggattgtaaa gttctgttgt tagggacaaa caagtaccgt     420
tcgaataggg cggtaccttg acggtacctg acgagaaagc cacggctaac tacgtgccac     480
cagccgcggt aatacgtagg tggcaagcgt tgtccggatt tattgggcgt aaagcgcgcg     540
caggcggcta tgtaagtctg gtgttaaagc ccggagctca actccggttc gcatcggaaa     600
ctgtgtagct tgagtgcaaa agaggaaagc ggtattccac gtgtagcggt gaaatgcgta     660
gagatgtgga ggaacaccag tggcgaaggc ggctttctgg tctgtaactg acgctgaggc     720
gcgaaagctg tggtggagca aacaggatta gataccctgc tagtccacgc cgtaaacgat     780
gagtgctagg tgttggggtt tcatacctca attgccgcag                          820
```